United States Patent [19]

Dunn et al.

[11] 4,308,251

[45] Dec. 29, 1981

[54] CONTROLLED RELEASE FORMULATIONS OF ORALLY-ACTIVE MEDICAMENTS

[75] Inventors: James M. Dunn; John F. Lampard, both of Shreveport, La.

[73] Assignee: Boots Pharmaceuticals, Inc., Nottingham, England

[21] Appl. No.: 194,453

[22] Filed: Oct. 17, 1980

Related U.S. Application Data

[63] Continuation-in-part of Ser. No. 111,430, Jan. 11, 1980, abandoned.

[51] Int. Cl.$^3$ .......................... A61K 9/22; A61K 9/30; A61K 9/52; A61K 9/56
[52] U.S. Cl. ......................................... 424/19; 424/21; 424/22; 424/39
[58] Field of Search ........................ 424/19, 20, 22, 39

[56] References Cited

U.S. PATENT DOCUMENTS

| | | | |
|---|---|---|---|
| 2,798,838 | 7/1957 | Robinson | 424/20 |
| 2,895,881 | 7/1959 | Harnada | 424/20 |
| 2,951,792 | 9/1960 | Swintosky | 424/20 |
| 2,953,497 | 9/1960 | Press | 424/20 |
| 2,993,836 | 7/1961 | Nash et al. | 424/20 |
| 3,039,933 | 6/1962 | Goldman | 424/20 |
| 3,065,143 | 11/1963 | Christenson et al. | 424/20 |
| 3,074,852 | 1/1963 | Mayron | 424/20 |
| 3,078,216 | 2/1963 | Greif | 424/20 |
| 3,080,294 | 3/1963 | Shepard | 424/20 |
| 3,081,233 | 3/1963 | Enz | 424/20 |
| 3,108,046 | 10/1963 | Harbit | 424/20 |
| 3,147,187 | 9/1964 | Playfair | 424/20 |
| 3,322,633 | 5/1967 | Simoons | 424/20 |
| 3,328,256 | 6/1967 | Gaunt | 424/22 |
| 3,330,729 | 7/1967 | Johnson, Jr. | 424/22 |
| 3,336,155 | 8/1967 | Rowe | 424/22 |
| 3,344,029 | 9/1967 | Berger | 424/22 |
| 3,362,880 | 1/1968 | Jeffries | 424/22 |
| 3,362,881 | 1/1968 | Eberhardt | 424/22 |
| 3,577,514 | 5/1971 | Robinson | 424/22 |
| 3,773,920 | 11/1973 | Nokamoto et al. | 424/19 |
| 3,906,086 | 9/1975 | Guy et al. | 424/20 |
| 3,965,256 | 6/1976 | Leslie | 424/22 |
| 4,012,498 | 3/1977 | Kornblum et al. | 424/22 |

Primary Examiner—Stanley J. Friedman
Attorney, Agent, or Firm—Gordon W. Hueschen

[57] ABSTRACT

An improved tablet formulation is provided comprising an effective amount of an active therapeutic agent, especially an acidic therapeutic agent such as aspirin, a release-controlling agent, and an erosion-promoting agent in relative amounts to provide a criticality factor of less than 450, and in proportions of release-controlling and erosion-promoting agent, respectively, between 0.8–1.6 and 1.0–7.5 weight percent per tablet. The tablets of this invention exhibit zero order release in vitro and closely approximate zero order absorption in vivo. The aspirin tablets of the invention produce minimal epigastric distress and can be administered twice-a-day to provide the desired therapeutic effect. The preferred release-controlling agent is cellulose acetate phthalate and the preferred erosion-promoting agent is corn starch.

25 Claims, 5 Drawing Figures

CONTROLLED RELEASE FORMULATIONS OF ORALLY-ACTIVE MEDICAMENTS

BACKGROUND OF INVENTION

This application is a continuation-in-part of our prior filed copending application Ser. No. 111,430, filed Jan. 11, 1980, now abandoned.

Field of Invention

Controlled-release tablets containing an orally-active therapeutic agent. Such tablets having enhanced controlled-release properties. Such tablets comprising both erosion-promoting and release-controlling agent. Such tablets wherein the therapeutic agent is of an acidic nature, especially a nonsteroidal arylalkanoic anti-inflammatory agent or aspirin.

Prior Art

Innumerable attempts have been made by the pharmaceutical art to provide controlled-release tablets of varying types, including such tablets as comprise, in addition to the active therapeutic agent, both erosion-promoting and release-controlling agents, since either of such agents alone have been found unsatisfactory in practice for most applications due to excessive erosion or excessive delay in release of the therapeutic agent. Nevertheless, although many contributions have been made in this art, such available controlled-release formulations leave much to be desired. For example, although erosion of the therapeutic agent is by itself sometimes adequate, so that an erosion-promoting agent may be omitted entirely, when an erosion agent is required together with a release-control agent, the tablet comprising both such ingredients plus the therapeutic agent must frequently be of excessive mass in order to obtain controlled-release properties, thus making production of a patient acceptable size tablet impossible or impractical. This area of the pharmaceutical art is accordingly in need of practical and reliable solutions to the problem of release-control tablets which do not suffer from the known disadvantages of previously available compositions of such type.

For example, aspirin, acetylsalicylic acid (ASA), including its salts and derivatives, e.g., its aluminum salt or its anhydricde, is acknowledged as the most widely used analgesic, antipyretic, and anti-inflammatory agent, and is the standard of reference and comparison for drugs with similar effects. See, for example, Goodman and Gilman, *The Pharmacological Basis of Therapeutics*, Fifth Edition, p. 326 (MacMillian Publishing Co., Inc., New York, 1975).

This compound is considered by many to be the drug of choice for the treatment of rheumatoid and osteoarthritis. However, side effects may be noted with moderate doses required for palliation of arthritic symptoms. These undesired side effects have limited the use of aspirin and have resulted in the development of alternative therapeutic agents. In the case of anti-inflammatory agents, a number of nonsteroidal arylalkanoic acids, e.g., phenylalkanoic, indolylacetic, biphenylalkanoic acids, their salts, and other derivatives have been developed in an effort to provide effective drug entities with lessened toxicity, e.g., indomethacin, fenoprofen, naproxen, ibuprofen, and flurbiprofen.

Approximately sixty percent of patients taking aspirin are considered treatment failures because of side effects. These untoward effects are epigastric distress, nausea, vomiting, gastric irritation, "silent" bleeding, exacerbation of peptic ulcer, gastrointestinal hemorrhage, erosive gastritis and even death. Although these findings are generally associated with high dose therapy, numerous patients canot tolerate aspirin even in lower dosages. This accounts for the success of acetaminophen products such as Tylenol(R) and Datril(R).

A further drawback of currently available aspirin formulations is the high number of tablets which must be ingested daily for certain treatment programs as well as the number of times dosing is required during each 24-hour period.

Although numerous attempts have been made to provide aspirin formulations which obviate the disadvantages, none of the commercially available aspirin products provide an ideal solution to the problem. In order to avoid gastric irritation, aspirin has been enterically coated with materials such as cellulose acetate phthalate. These materials are resistant to acid pH, but dissolve in basic pH. Thus, drug is released once out of the stomach. However, significant blood levels are achieved only after dissolution, about one to two hours after ingestion. Sustained release is not provided with these formulations. The aspirin tablet, once the enteric coating has dissolved, releases acetylsalicylic acid in a single slug and additional drug has to be taken in another four hours.

Aspirin has also been buffered or combined with an antacid in attempts to reduce gastric irritation. These formulations do not reduce the number of aspirin tablets needed daily, nor the frequency with which the product must be taken. Further, they have not provided a satisfactory solution to the problem of gastrointestinal irritation and bleeding.

Sustained release formulations have been prepared in a variety of ways. The majority of commercially available sustained release preparations consist of micro-encapsulated drug which may be presented as capsules or tablets. Cellulose acetate phthalate may be one of the materials used in such preparations. These sustained release formulations do not solve the problem of gastric irritaion, nor do they provide a zero order release pattern or approximate a zero order absorption profile. It should be further noted that a twice-a-day dosing regimen is not available with any commercially available aspirin product.

Numerous prior art patents are directed to providing sustained release aspirin formulations. The prior art attempts to provide sustained release aspirin formulations failed to recognize and solve the problem of gastric irritation and also failed to provide an aspirin formulation which can be administered only twice-a-day.

Press, U.S. Pat. No. 2,953,497, teaches a complicated procedure for the preparation of time-release granules by mixing one part of the active ingredient, i.e., aspirin, with 2 parts of powdered sucrose and 5–10 parts of corn starch, granulating the mixture with corn syrup, dividing the granules into a plurality of batches and coating each batch with shellac or cellulose acetate phthalate solutions of different concentrations to provide granules having different disintegration rates. Press had no appreciation for the problems involved in providing an aspirin formulation which would overcome the problems of epigastric distress, et cetera, and provie a controlled release product in tablet form which can be administered only twice-a-day to provide sustained blood levels.

Gun, U.S. Pat. No. 3,906,086, while directed to a multilayer tablet having one layer of conventional aspirin and one layer of delayed release material, discloses coating particles of aspirin prior to tableting with a coating solution containing cellulose acetate phthalate, preferably with a plasticizer. Guy omits the use of any pharmaceutical excipients such as corn starch or a similar erosion-promoting agent, failing to recognize the criticality of the presence of an erosion-promoting agent and of the relative amounts of aspirin, cellulose acetate phthalate and starch required for achieving the desired delayed-release without regard to tablet hardness.

Kornblum, U.S. Pat. No. 4,012,498 and Harbit, U.S. Pat. No. 3,108,046, also broadly disclose the concept of coating granules with a solution of sustained release material and subsequently compressing the coated granules into tablets, as does Eberhardt, U.S. Pat. 3,362,881, these efforts being directed toward specific different problems or resulting only in tablets of an impractical size which is, however, essential to obtain sustained release properties.

Therefore, although the broad concept of coating and compressing aspirin and other oral therapeutic agents into controlled-release tablets has been known, the present invention provides a significant and highly desirable advance over the prior art.

OBJECTS

It is threfore an object of the present invention to provide controlled-release tablets containing both erosion-promoter and release-control agent which are well adapted to meet the needs of the pharmaceutical art and avoid the disadvantages of such previously-available tablet compositions as set forth in the foregoing. Another object is to provide such compositions which, upon oral administration, provie delayed disintegration rates, prolonged dissolution times, and sustained blood levels of the orally active therapeutic agent involved. A further object is to provide such a tablet without excessive bulk and having weight and size characteristics which make it well-adapted for practical and acceptable patient administration. Other objects will be apparent to one skilled in the art and still others will become apparent as this application proceeds.

SUMMARY OF THE INVENTION

We have now surprisingly found that, by carefully controlling the relative amounts of therapeutic agent, e.g., aspirin, a release-controlling agent which is resistant to acidic pH, and an erosion-promoting agent which aids in tablet disintegration, so that a criticality factor of between 20 to 450 is achieved, and by maintaining the proportions of 0.8 to 1.6 weight percent per tablet of the release-controlling agent and 1.0 to 7.5 weight percent per tablet of the erosion-promoting agent, a superior controlled-release tablet product is obtained without regard for tablet hardness within a broad range. Other non-interfering materials or ingredients, which do not adversely interfere with attainment of the objectives of the invention or with the controlled-release characteristics of the tablet thus produced, may also be included if desired, but the three components just recited, and in the relative proportions recited, are essential according to the present invention.

Advantageously, the tablet product of the present invention can be prepared using standard methods and equipment. Briefly, the therapeutic agent is intimately mixed with the erosion-promoting agent. A solution of the release-controlling agent is added to the medicament-erosion-promoting agent mixture to form a wet granular mass. The mass is dried, reduced to the desired particle size, and compressed into tablets.

The tablet product of this invention exhibits a zero order release profile in vitro and closely approximates zero order absorption in vivo. The aspirin tablet formuation of the invention can thus be administered twice a day to provide sustained therapeutic effect without gastric irritation.

DETAILED DESCRIPTION OF THE INVENTION

The tablet formulation of the present invention comprises an effective amount of the medicament, i.e., the therapeutic agent, a release-controlling agent, and an erosion-promoting agent in amounts providing a criticality factor of less than 450, preferably between 20 and 450. The preferred criticality factor range is between 80 and 330, preferably between 210 and 330, calculated according to the formula:

$$CA/(1/CS)=CF$$

wherein: CA is the content of medicament (mg/tablet) divided by the content of release-controlling agent (mg/tablet), CS is the content of erosion-promoting agent (mg/tablet) divided by the content of release-controlling agent (mg/tablet), and CF is the criticality factor. While the amounts of erosion-promoting and release-controlling agent can be varied within limits, it is also necessary to employ about 0.8 to about 1.6 weight percent per tablet of release-controlling agent, preferably about 1.15 to about 1.6 weight percent, and about 1.0 to about 7.5 weight percent per tablet of erosion-promoting agent, preferably about 2.0 to about 5.0 weight percent per tablet.

Formulations according to the present invention, having a cricitcality factor value between 20 and 450 and the required proportions of erosion-promoting and release-control agents, provide compressed medicament tablets which exhibit zero order release kinetics in vitro and closely approximate zero order absorption kinetics in vivo. When aspirin is the medicament, they can be administered twice-a-day for prolonged therapeutic effect and their use is not characterized by the extreme gastric irritation common with standard aspirin products.

Generally speaking, it is preferred to formulate tablets according to the present invention containing 650 to about 800 mg of aspirin per tablet. Tablets containing greater amounts of aspirin can be formulated, but are seldom patient-acceptable.

For tablets containing 650 to about 800 mg of aspirin per tablet, generally speaking, about 5.0 to about 13.6 mg of a release-controlling agent and about 13.4 to about 63.8 mg of an erosion-promoting agent per tablet are employed as preferred amounts providing the desired criticality factor and proportions.

The preferred release-controlling agent is cellulose acetate phthalate. Other suitable release-controlling agents include but are not limited to cellulose acetate derivatives disclosed in Hiatt U.S. Pat. No. 2,196,768, shellac, zein, acrylic resins, ethylcellulose, hydroxypropylmethylcellulose phthalate, sandarac, modified shellac, and so forth.

The preferred erosion-promoting agent is corn starch. Other suitable erosion-promoting agents include, but are not limited to, rice starch, potato starch and other equivalent vegetable starches, modified starch and starch derivatives, cellulose derivatives and modified cellulose or derivatives, e.g., methylcellulose, sodium carboxymethylcellulose, alginic acid and alginates, bentonite, veagum, cross-linked polyvinylpyrrolidone, ion-exchange resins, and gums, e.g., agar, guar, and so forth.

Generally speaking, the medicament tablets of the present invention are prepared by dissolving the release-controlling agent in a suitable organic solvent or solvent mixture such as methylene chloride and denatured alcohol [1:1(v/v)]. Other suitable solvents include but are not limited to lower-aliphatic alcohols such as methanol, iso-propanol, n-propanol, et cetera, acetone and lower-aliphatic ketones such as methyl ethyl ketone, chloroform, carbon tetrachloride, ethyl acetate and non-chlorinatedhydrocarbons.

The selected medicament, e.g., aspirin USP, preferably in the form of 40 mesh/inch crystals or 80 mesh/inch powder, is intimately mixed with the erosion-promoting agent, preferably corn starch. The solution of the release-controlling agent, preferably of cellulose acetate phthalate, is added to the mixing powders in a steady stream and mixing is continued to form a wet granular mass. The wet mass is dried to remove residual organic solvent, leaving the release-controlling agent in intimate contact with the primary particles of the medicament, e.g., aspirin, and erosion-promoting agent. The granular mass is reduced to a suitable granule size by forcing the material through a 14–20 mesh/inch screen. The dry granules are blended to ensure homogeneity and then compressed into tablets using a conventional rotary or single station tablet press. The tablets may then be printed directly using conventional tablet printing equipment and materials to identify the product. Tablet identification may also be made by debossing the finished product during compression.

The medicament tablets so produced exhibit superior controlled-release characteristics, greater stability than currently available tablet products, and can accept print directly on the finished product without treatment with waxes, coating, or polishing. Aspirin tablets of the invention do not have the proclivity for gastro-intestinal irritation noted with regular soluble aspirin, and provide an aspirin product which exhibits zero order release kinetics in vitro and approximates zero order absorption kinetics in vivo. Because of their superior controlled-release properties, aspirin tablets of the present invention can be administered twice-a-day to provide the desired therapeutic effect.

The following examples further illustrate the present invention, but are not to be construed as limiting.

EXAMPLE 1

Cellulose acetate phthalate (67.3 g) was added slowly to the vortex of a mixture of ethanol (denatured, 625 ml) and methylene chloride (175 ml) produced by a high speed stirrer. Stirring was continued until solution was achieved.

Aspirin (4.375 kg, 40 mesh/inch crystal, USP) and corn starch (0.2255 kq, USP) were deaggregated through a 40 mesh/inch screen into the bowl of a Hobart mixer. The dry powders were mixed for five minutes at speed 1. The cellulose acetate phthalate solution was added to the mixing powders over a thirty-second period, with mixing at speed 1. Further mixing for four minutes at speed 2 was carried out to promote granulation.

The wet granular mass was discharged onto stainless steel trays and air dried until it could be forced through a 20 mesh/inch screen. The screened granulate was further air dried to remove residual solvent. The granules were weighed, blended by tumbling, and compressed on a conventional rotary tablet press using half-inch flat bevelled edge tooling to produce tablets containing 650 mg of aspirin with a hardness of 8 to 10 Kp (Schleuniger).

EXAMPLE 2

Cellulose acetate phthalate (750 g) was added slowly to the vortex of a mixture of methylene chloride (3750 ml) and ethanol (3750 ml). Stirring was continued until solution was achieved.

Aspirin (60 kg, 80 mesh per inch powder, USP) and corn starch (3.0 kg, USP) were placed in the bowl of a Littleford MGT 400 mixer. The dry powders were mixed using the impeller at speed 1 for two minutes. The cellulose acetate phthalate solution was poured in a steady stream onto the powders mixing at impeller speed 1 and chopper speed 1. Following addition of the solution, mixing was continued at impeller and chopper speed 2 until a suitable granular mass was obtained. The wet granular mass was spread on stainless steel trays and dried in a forced convection oven at a temperature not greater than 120° F. The dry granular mass was processed through a Jackson Crockatt granulator carrying a stainless steel screen of 16 mesh/inch. The dried sized granules were blended in a drum blender for five minutes, and compressed on a conventional rotary tablet press using capsule shaped tooling to give tablets containing 800 mg of aspirin with a hardness of 8 to 11 Kp (Schleuniger).

EXAMPLES 3-9

In order to demonstrate the direct relationship between the numerical value of the criticality factor and the speed of tablet disintegration, six formulations were prepared as described above in Example 1 and compared with a conventional aspirin tablet. The results are set forth in Table 1.

TABLE 1

| Example | Composition (mg/tablet) | | Criticality Factor (CF) | Disintegration* Time (pH 7.5 buffer) | Release Property (dissolution)** |
|---|---|---|---|---|---|
| 3 | Aspirin | 650 | 87 | >180 minutes | zero order |
|   | Starch  | 13.4 |  |  |  |
|   | CAP     | 10 |  |  |  |
| 4 | Aspirin | 650 | 348 | >240 minutes | zero order |
|   | Starch  | 13.4 |  |  |  |
|   | CAP     | 5 |  |  |  |
| 5 | Aspirin | 800 | 480 | 60 minutes | insufficient sustained release |
|   | Starch  | 60 |  |  |  |
|   | CAP     | 10 |  |  |  |
| 6 | Aspirin | 800 | 1333 | <5 minutes | no prolonged in vitro disintegration |
|   | Starch  | 60 |  |  |  |
|   | CAP     | 6 |  |  |  |
| 7 | Aspirin | 800 | 320 | >210 minutes | zero order |
|   | Starch  | 40 |  |  |  |
|   | CAP     | 10 |  |  |  |
| 8 | Aspirin | 650 | Conventional aspirin | <20 seconds non-buffered | instant |
|   | Starch  | 65 |  |  |  |
| 9 | Aspirin | 650 | 218 | >180 minutes | zero order |
|   | Starch  | 33.5 |  |  |  |
|   | CAP     | 10 |  |  |  |

In the above Examples, CAP stands for cellulose acetate phthalate and starch refers to corn starch.
*Determined by USP XX, page 958 procedure, without discs.
**Determined by USP XX, page 959 procedure, using a modified Apparatus 1 having a propeller mounted on the shaft above the basket.

EXAMPLES 10-13

The volume of the release-controlling agent must be sufficient to provide a wetted powder mass with liquid bridges. Although overwetting of the powder mass is not critical to the release characteristics of the compositions of the invention, provided the criticality factor and proportions are not exceeded, the further processing of material is rendered more difficult. Underwetting would not allow formation of a liquid bridge state and the subsequent formation of a granular mass in which the ingredients are intimately mixed. As is common in granulation of pharmaceutical products, the relative volume of fluid employed in forming the required wet granular mass and subsequent granulation decreases on increasing the size of the batch.

Table 2 demonstrates the interrelationship between the ingredients of the composition and the solution volume on wetting.

TABLE 2

| | Aspirin-starch(Kg) | CAP solution volume | g/ml |
|---|---|---|---|
| 10. | 0.446 | 80 ml | 5.58 |
| 11. | 4.6 | 800 ml | 5.75 |
| 12. | 6.835 | 900 ml | 7.59 |
| 13. | 63 | 7.5 L | 8.4 |

The ratio of the preferred solvents, methylene chloride: denatured ethanol may be varied, but should generally not exceed 1:3.57 (v/v) as solution of cellulose acetate phthalate becomes extremely difficult in such cases. The preferred ratio is 1:1.

The tablets of this invention have good physical strength and show zero-order release properties over a range of tablet hardness. The preferred range of hardness is between 7 and 11 Kp (Schleuniger).

EXAMPLE 14

The friability of the tablets of this invention is good with typical percentage weight loss following 100 drops in a Roche friabilator of between 0.12 and 0.46 weight percent per tablet at a tablet hardness of between 7 and 11 Kp. Prolongation of the test to give 750 total drops produced worn edges but did not break up the tablets. Typical results obtained with a commercial sustained release aspirin product were:
100 drops: 0.85% weight loss
750 drops: severely worn tablets

EXAMPLE 15

Disintegration in simulated gastric juice (buffer pH 1.2 plus pepsin) at 37° C. leaves a residue of between 70 and 80% of the original tablet weight after 2 hours.

EXAMPLES 16-19

Disintegration of aspirin tablets of this invention in a buffer of pH 7.5 produced the following results shown in Table 3:

TABLE 3

| | ASA mg/tablet | Example No. | CF | Mean Disintegration Time (min) | Residue % | Tablet Hardness (Kp) |
|---|---|---|---|---|---|---|
| 16. | 650 | 3 | 87 | >180 | 5.5 | 17.1 ± 0.97 |
| 17. | 650 | 9(Batch a) | 218 | >180 | 6.1 | 9.7 ± 0.81 |
| 18. | 800 | 7 | 320 | >210 | 29.1 | 8.3 ± 0.79 |
| 19. | 650 | 4(Batch a) | 348 | >240 | 14.1 | 10.3 ± 1.26 |

ASA = acetylsalicyllic acid

The disintegration in buffer is characterised by a slow and steady erosion of the tablet mass.

EXAMPLES 20-23

The dissolution of acetylsalicylic acid from the tablets of this invention has been assessed by two methods:* (a) single solution dissolution at pH 7.5 as set forth in Table 4.
*Both methods were according to USP XX, page 959 procedure, using a modified apparatus 1 having a propeller mounted on the shaft above the basket.

TABLE 4

| | ASA/tablet (mg) | Example | CF | Tablet Hardness (Kp) | Amount of ASA Released at Time Shown | | |
|---|---|---|---|---|---|---|---|
| | | | | | Time (min) | mg | % |
| 20. | 650 | 3 | 87 | 17.1 ± 0.97 | 60 | 189 | 29.1 |
|  |  |  |  |  | 180 | 467 | 71.8 |
|  |  |  |  |  | 300 | 640 | 98.5 |
| 21. | 650 | 9 (Batch b) | 218 | 9.6 ± 1.09 | 60 | 204 | 31.3 |
|  |  |  |  |  | 180 | 469 | 72.2 |
|  |  |  |  |  | 300 | 651 | 100.2 |
| 22. | 800 | 7 | 320 | 8.3 ± 0.79 | 60 | 229 | 28.6 |
|  |  |  |  |  | 180 | 574 | 71.8 |
|  |  |  |  |  | 300 | 783 | 97.9 |
| 23. | 650 | 4 (Batch b) | 320 | 7.6 ± 1.63 | 60 | 241 | 30.1 |
|  |  |  |  |  | 180 | 598 | 74.8 |
|  |  |  |  |  | 300 | 798 | 99.8 |

EXAMPLES 24-25

The dissolution of acetylsalicylic acid from the tablets of Examples 9 and 3 were assessed in a second method:* (b) involving pH change. The results are set forth in Table 5.

*Both methods were according to USP XX, page 959 procedure, using a modified apparatus 1 having a propeller mounted on the shaft above the basket.

TABLE 5

| Time (hrs) | Initial pH | mg ASA released by end of time | | Cumulative amount ASA released(mg) | | % of Theory ASA released | |
|---|---|---|---|---|---|---|---|
| | | Ex. 9* | Ex. 3 | Ex. 9* | Ex. 3 | Ex. 9* | Ex. 3 |
| 0-½ | 1.2 | 50 | 46 | 50 | 46 | 7.7 | 7.1 |
| 0-1 | 1.2 | 72 | 60 | 72 | 60 | 11.1 | 9.2 |
| 1-3 | 4.4 | 125 | 96 | 197 | 156 | 30.3 | 24.0 |
| 3-6.5 | 7.5 | 410 | 425 | 607 | 581 | 93.4 | 89.4 |

*Batch b
Example 24 represents data from tablet Example 9.
Example 25 represents data from tablet Example 3.

The data of Examples 20-25 show a sustained and essentially zero order release for the formulations of this invention. They also show that the tablet hardness is not critical in obtaining a satisfactory release profile. Tablets with a hardness of 9.6 or 17.1 Kp show similar profiles. This property facilitates uniformity from production, inasmuch as any machine-induced hardness variation will not adversely affect the release profile of the final product.

EXAMPLES 26-27

The stability of the tablets of the present invention is enhanced. The level of chemical degradation which occurs on storage is less than that occuring with conventional aspirin formulations. Acetyl salicylic acid degrades to salicylic acid, and this reaction is promoted by elevated temperature. The reaction occurs readily and has led to the adoption by the U.S. Pharmacopeia of an upper limit for the level of free salicylic acid (FSA) in aspirin tablets at 0.3%.

Tablets formulated according to the method of Example 1 were assayed for FSA following extreme storage conditions with the results set forth in Table 6.

TABLE 6

| Time | Storage Temperature | Level of FSA % |
|---|---|---|
| Initial | — | 0.04 |
| 3 months | 40° C. | 0.12 |

It is widely known that, under similar conditions of storage, the limiting level of FSA, viz., 0.3%, would be exceeded by conventional aspirin formulations.

Additionally, tablets formulated according to the method of Example 7 were assayed for FSA following extreme storage conditions with the results shown in Table 6A.

TABLE 6A

| Time | Storage Condition | Level of FSA % |
|---|---|---|
| Initial | — | 0.06 |
| 6 months | 40° C. | 0.14 |
| | 37° C./75% RH | 0.22 |

EXAMPLE 28

Serum Levels After a Single Oral Dose

Figure 1:
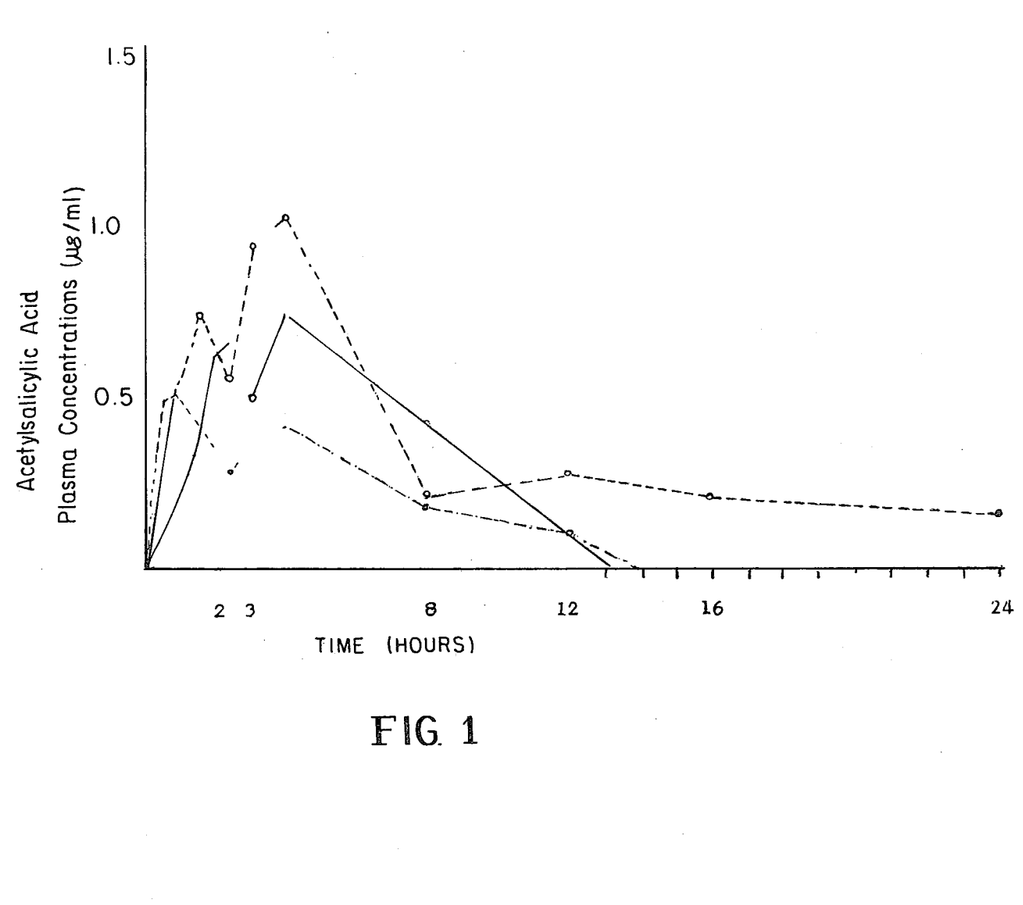
FIG. 1 is a graphical illustration of the results of the test described in Example 28 showing serum levels of aspirin (acetylsalicylic acid) over a 24-hour period in each of two subjects receiving two 650 m tablets as a single 1300 mg dose of aspirin, the tablets being in accordance with this invention (unbroken and broken lines), as compared with a single 650 mg tablet, also in accord with the invention (alternate dot and dash line).

Tablets containing 650 mg of aspirin were produced according to the method of Example 1. One human volunteer was given a single oral dose of 650 mg while two other individuals received a single dose of 1300 mg (two 650 mg tablets). Blood samples were taken from each subject via an indwelling catheter from a vein in the forearm. The samples were collected in a chilled vacutainer tube at the following times: prior to dosing and at 15, 30, 45 and 60 minutes; 1.5, 2.0, 2.5, 3.0, 4.0, 8.0, 12.0, 16.0, and 24 hours post dose. The blood samples were analyzed for plasma salicylic acid and acetylsalicylic acid using high pressure liquid chromatography. The following table and FIG. 1 show the results of these measurements.

TABLE 7

Plasma Acetylsalicylic Acid and Salicylic Acid Values over a 24-hour Period

| | Subject Nos.: | | | | | |
|---|---|---|---|---|---|---|
| | 1 | | 2 | | 3 | |
| | Aspirin Doses: | | | | | |
| | 1300 mg mcg/ml | | 650 mg mcg/ml | | 1300 mg mcg/ml | |
| Study Time | ASA | SA | ASA | SA | ASA | SA |
| 0 | 0.1 | 0.1 | 0.1 | 0.1 | 0.1 | 0.1 |
| 15 | 0.1 | 0.38 | 0.1 | 0.1 | 0.1 | 0.2 |
| 30 | 0.1 | 0.93 | 0.1 | 0.1 | 0.46 | 0.99 |
| 45 | 0.43 | 1.58 | 0.1 | 0.28 | 0.49 | 1.81 |
| 1 | 0.41 | 2.18 | 0.19 | 0.67 | 0.53 | 2.26 |
| 1.5 | 0.37 | 3.19 | 0.35 | 1.53 | 0.71 | 3.24 |
| 2.0 | 0.59 | 4.30 | 0.30 | 2.45 | 0.61 | 4.07 |
| 2.5 | 0.61 | 5.55 | 0.25 | 3.08 | 0.51 | 4.99 |
| 3.0 | 0.46 | 5.70 | 0.35 | 3.29 | 0.89 | 6.01 |
| 4.0 | 0.68 | 8.89 | 0.38 | 4.27 | 0.97 | 10.70 |
| 8.0 | 0.39 | 17.00 | 0.18 | 5.47 | 0.20 | 11.30 |
| 12.0 | 0.1 | 17.90 | 0.1 | 3.72 | 0.26 | 19.30 |
| 16.0 | 0.1 | 8.87 | 0.1 | 3.83 | 0.20 | 14.00 |
| 24.0 | 0.1 | 0.36 | 0.1 | 2.96 | 0.17 | 9.24 |

The serum levels of acetylsalicylic acid were shown to peak, in all three subjects, four hours after drug ingestion. Levels did not return to 0.1 microgram/milliliter until after eight hours. This finding is to be compared to the established half life (t=½) of twenty minutes for serum acetylsalicylic acid following administration of a standard 650 mg aspirin tablet.

EXAMPLE 29

Serum Levels Following Multiple Oral Doses

Figure 2:
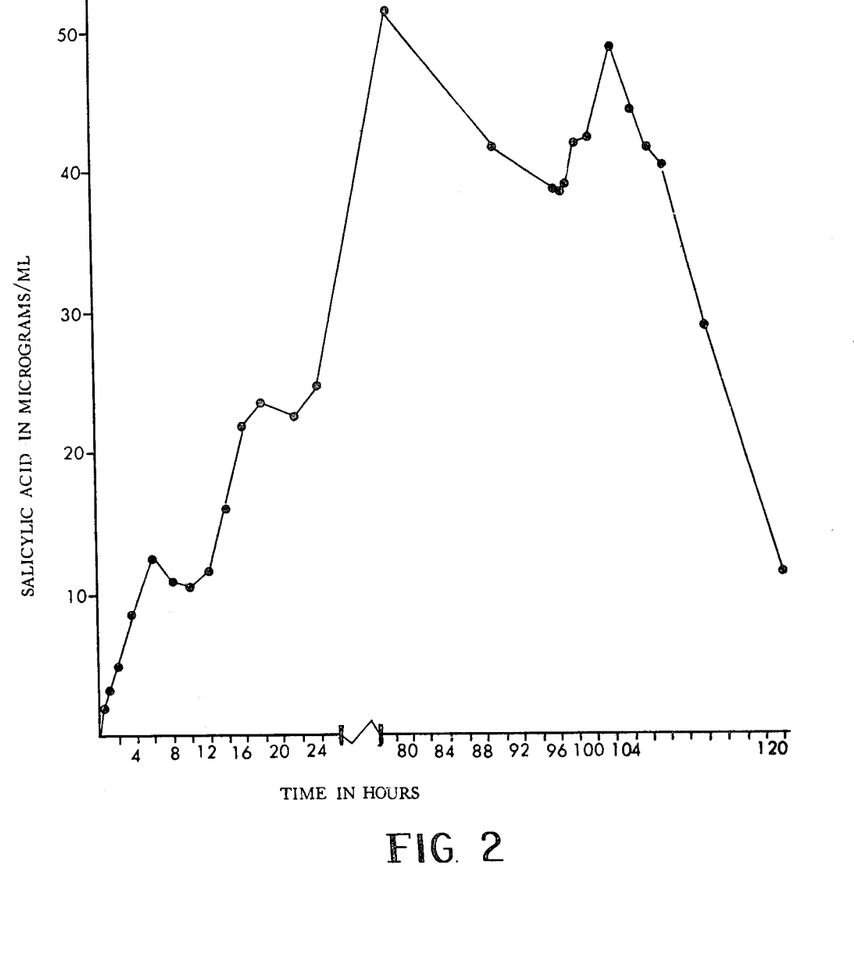
FIG. 2 is a graphical illustration of the results of the test described in Example 29 showing serum levels of salicylic acid over a 120-hour period involving multiple oral doses (nine doses-each 2×650 mg—12 hours apart over a 96-hour period) of aspirin tablets in accordance with this invention in eight subjects, the blood samples being taken at the hours indicated.
Figure 3:
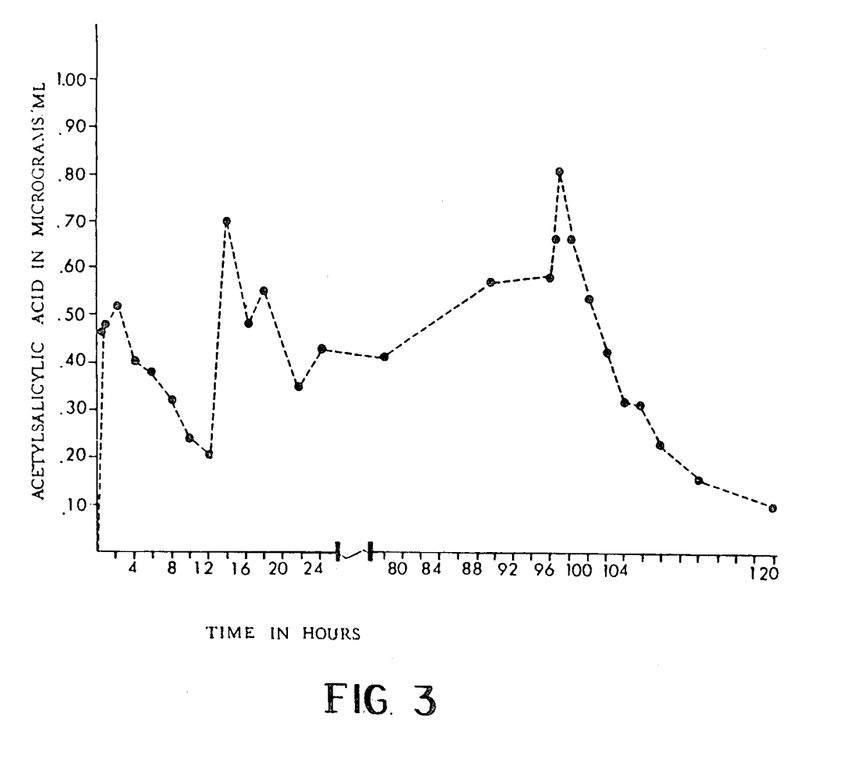
FIG. 3 is a graphical illustration of the results of the test set forth in Example 29 and described for FIG. 2 showing serum levels of aspirin (ASA).

Aspirin tablets prepared according to the method of Example 1 were administered orally to eight healthy volunteers in doses of 1300 mg (two 650 mg tablets) twice-a-day at 0800 and 2000 hours for nine consecutive doses, the last dose being given on the 96th hour, to determine the steady-state pharmacodynamics of the aspirin tablet formulation of this invention. Blood samples were taken from the subjects at predetermined time intervals during the course of the study. The blood samples were analyzed by high performance liquid chromatography for levels of salicylic acid and acetylsalicylic acid. Individual blood levels of salicylic acid and acetylsalicylic acid found on Day five of the study are shown in Tables 8 and 9. Graphical representation of the mean blood levels for salicylic acid and acetylsalicylic acid for the entire study are shown in FIGS. 2 and 3, respectively.

TABLE 8

Salicylic Acid Levels on Day Five, mcg/ml

| Sub No. | Time (hrs) Post Dose | | | | | | | | | | |
|---|---|---|---|---|---|---|---|---|---|---|---|
| | 0 | 0.5 | 1 | 2 | 4 | 6 | 8 | 10 | 12 | 16 | 24 |
| 1 | 9.37 | 9.98 | 10.05 | 10.93 | 13.38 | 18.33 | 15.03 | 12.73 | 10.41 | 8.31 | 1.58 |
| 2 | 63.85 | 68.23 | 73.98 | 77.12 | 72.08 | 89.96 | 75.93 | 79.22 | 85.07 | 75.04 | 43.32 |
| 3 | 80.3 | 78.57 | 83.41 | 90.31 | 87.82 | 94.47 | 85.67 | 74.27 | 64.84 | 37.83 | 9.91 |
| 4 | 72.48 | 68.78 | 62.69 | 62.63 | 67.49 | 67.48 | 60.04 | 49.41 | 52.85 | 40.19 | 16.87 |
| 5 | 38.37 | 32.39 | 31.42 | 30.78 | 28.39 | 34.27 | 33.51 | 34.42 | 35.16 | 31.37 | 12.16 |
| 6 | 22.85 | 24.81 | 25.26 | 28.80 | 28.09 | 30.22 | 29.61 | 30.54 | 36.95 | 15.36 | 2.70 |
| 7 | 11.98 | 14.53 | 15.98 | 20.90 | 24.47 | 33.42 | 35.19 | 35.47 | 34.07 | 10.35 | 0.40 |
| 8 | 10.65 | 12.04 | 13.98 | 16.57 | 18.61 | 24.01 | 19.52 | 15.93 | 15.58 | 13.78 | 3.59 |
| Mean | 38.73 | 38.67 | 39.60 | 42.26 | 42.54 | 49.02 | 44.31 | 41.50 | 40.62 | 29.03 | 11.31 |
| ±SEM | 10.45 | 10.10 | 10.34 | 10.64 | 10.09 | 10.74 | 9.30 | 8.70 | 8.97 | 7.93 | 5.01 |

TABLE 9

Acetylsalicylic Acid Levels on Day Five, mcg/ml

| Sub No. | Time (hrs) Post Dose | | | | | | | | | | |
|---|---|---|---|---|---|---|---|---|---|---|---|
| | 0 | 0.5 | 1 | 2 | 4 | 6 | 8 | 10 | 12 | 16 | 24 |
| 1 | 0.15 | 0.39 | 0.43 | 0.47 | 0.49 | 0.31 | 0.34 | 0.46 | 0.22 | 0.18 | 0.09 |
| 2 | 0.81 | 1.07 | 1.97 | 0.76 | 0.47 | 0.32 | 0.28 | 0.47 | 0.28 | 0.16 | 0.09 |
| 3 | 0.79 | 0.76 | 0.75 | 0.66 | 0.40 | 0.28 | 0.05 | 0.05 | 0.05 | 0.05 | 0.10 |
| 4 | 1.08 | 0.65 | 0.88 | 0.65 | 0.95 | 0.63 | 0.43 | 0.26 | 0.43 | 0.26 | 0.09 |
| 5 | 0.74 | 0.59 | 0.49 | 0.55 | 0.32 | 0.89 | 0.43 | 0.24 | 0.25 | 0.23 | 0.18 |
| 6 | 0.23 | 0.80 | 0.62 | 0.89 | 0.35 | 0.31 | 0.43 | 0.46 | 0.28 | 0.16 | 0.09 |
| 7 | 0.15 | 0.41 | 0.50 | 0.54 | 0.75 | 0.28 | 0.30 | 0.37 | 0.19 | 0.08 | 0.09 |
| 8 | 0.65 | 0.65 | 0.86 | 0.80 | 0.62 | 0.43 | 0.33 | 0.19 | 0.13 | 0.16 | 0.09 |
| Mean | 0.58 | 0.67 | 0.81 | 0.67 | 0.54 | 0.43 | 0.32 | 0.31 | 0.23 | 0.16 | 0.10 |
| ±SEM | 0.12 | 0.08 | 0.18 | 0.51 | 0.08 | 0.08 | 0.04 | 0.54 | 0.04 | 0.02 | 0.01 |

EXAMPLE 30

Evaluation in Patient No. 1

S.W. is a 32 year old white female housewife who suffered a painful right shoulder for two years. Consultants believed this condition was a result of chronic bursitis. Various analgesics were tried for the two-year period with only intermittent and partial relief. Aspirin as regularly prescribed was ineffective and caused epigastric discomfort. The patient was given oral aspirin, formulated according to Example 1, 1300 mg (2×650 mg) twice-a-day. After four days the pain had diminished to an insignificant level. She has been maintained on this therapy for six weeks and has increased the range of motion in the right shoulder and has had no further recurrences of pain.

EXAMPLE 31

Evaluation in Patient No. 2

M.H. is a 42 year old white female who is employed full time in an accounting department of a small company. She has had a ten year history of aspirin intolerance manifested by epigastric pain, nausea and burning with occasional diarrhea. While skating she fell, causing a partial tear of the medial collateral ligament and medial meniscus of the left knee. Support wrappings and acetaminophen were tried. Pain relief was only partial and temporary with regular acetaminophen. Despite the patient's previous history of aspirin intolerance, she was given aspirin tablets formulated according to Example 7, 1600 mg (2×800 mg tablets) twice daily by mouth. Immediate relief was not observed, but 10–12 hours following the first dose there was only minimal pain and the patient could walk without assistance. This dosage regimen was maintained throughout the patient's convalescence. She reported no epigastric discomfort, nausea, or abdominal pain while taking this aspirin formulation.

EXAMPLE 32

Evaluation in Patient No. 3

W.H., a 33 year old white male, sustained a traumatic injury to the medial portion of his right knee during a basketball game. He had a history of epigastric discomfort and sensitivity to aspirin products. In the afternoon on the day of his injury, he was given aspirin (650 mg) compounded according to Example 1. He continued to have moderate pain, "until sometime during the night". Ten hours following the first dose of aspirin he reported only mild pain and was ambulating well. He remained on this aspirin formulation twice-a-day for ten days, 650 mg per dose, and remained free of significant pain despite evidence of swelling and bruising about the injury site.

EXAMPLE 33

Comparison of Aspirin Absorption to a Simulated Zero Order Curve

To demonstrate the close proximity of the in vivo absorption profile of aspirin formulated according to the present invention, the data of subject 1 of Example 29 was compared to an ideal, simulated zero order curve.

Figure 4:
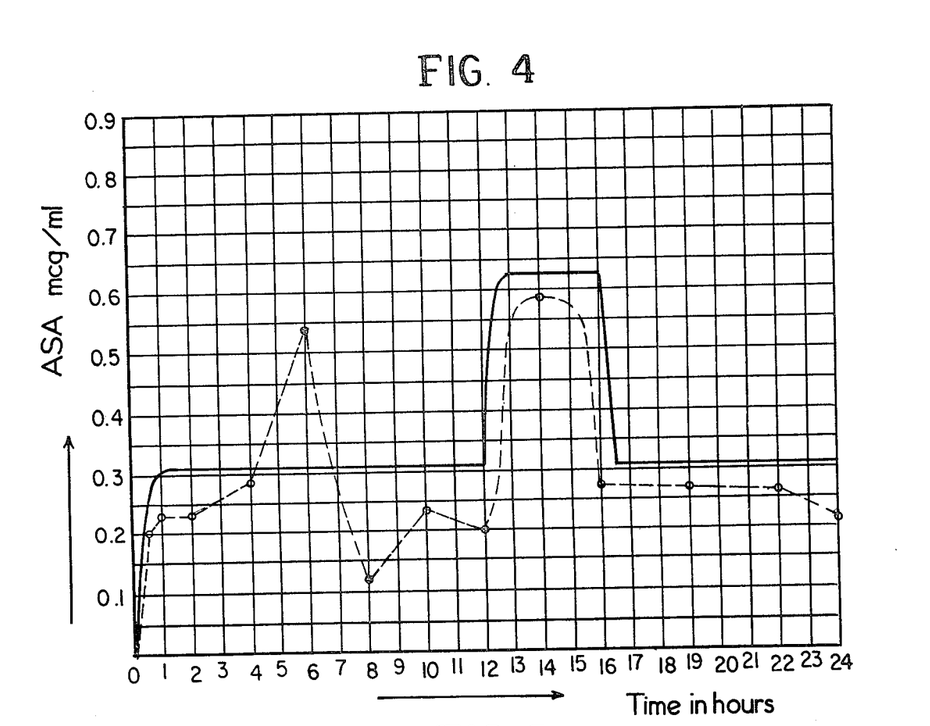
FIG. 4 is a graphical illustration of the results of a comparison between a simulated computer curve for zero order absorption of aspirin (solid line) and the actual values from blood samples taken on Day 1 of treatment for subject 1 (dotted line) from Example 29.

The results are shown in FIG. 4. The computer-simulated curve is shown as a solid line and the subject data as a dotted line.

EXAMPLE 34

Comparison of Aspirin Absorption to Simulated Zero Oral Absorption Curve (Second Comparison)

Figure 5:
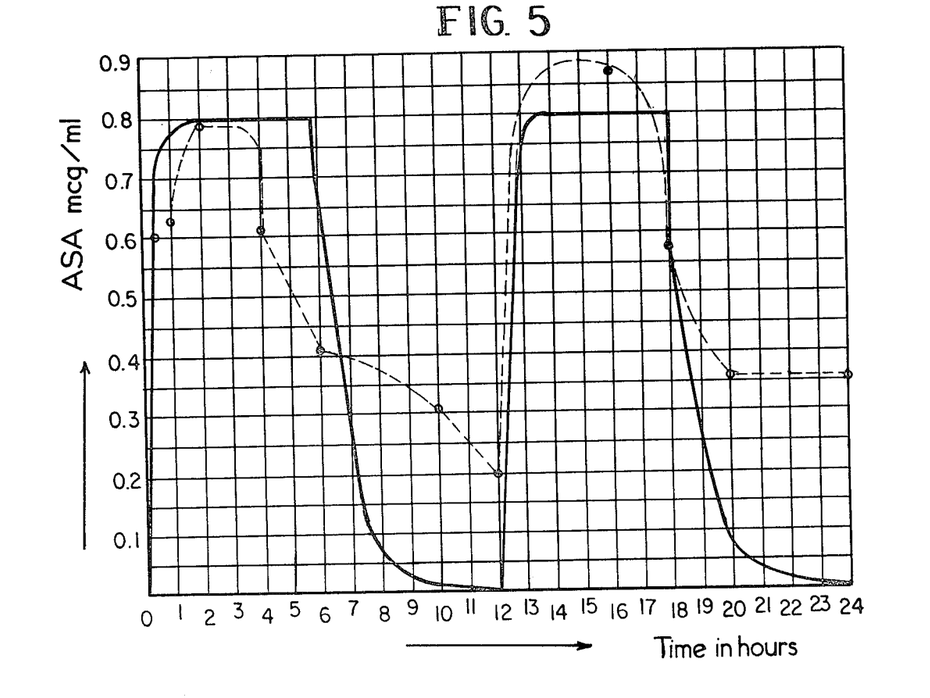
FIG. 5 is a grahical illustration of the results of a comparison between the theoretical value for zero order absorption of aspirin (solid line) in a second subject and the actual values from blood samples taken on Day 1 of treatment for subject 2 (dotted line) from Example 29.

To further demonstrate the close proximity of the in vivo absorption of aspirin formulated according to the present invention, the data of subject 2 of Example 29 was compared to an ideal, simulated zero order curve. The results are shown in FIG. 5. The computer-simulated curve is shown as a solid line and the subject's data as a dotted line.

The simulated zero order curves for FIGS. 4 and 5 were calculated based on a two-compartment model with first order metabolism. The rate constants were taken from Rowland and Riegelman, *J. Pharm. Sci.*, Vol. 57, page 1313 (1968).

wherein ASA is acetylsalicylic acid and SA is salicylic acid.

This model assumes about 60% of the acetylsalicylic acid passes the liver unhydrolyzed and the rate of entry is constant over the time T required for the entire dose to be absorbed. If the T=16 hours, then the 650 mg dose reaches the liver (portal circulation) at 650/16=40.63 mg/hr, of which 60% (24.4 mg/hr) reaches the general circulation as acetylsalicylic acid. To the extent that T is a variable, it will alter the rate and the extent to which multiple doses overlap one another.

FIG. 4 shows reasonable agreement with a zero order simulation over sixteen hours and FIG. 5 shows reasonable agreement with a zero order simulation of six hours absorption time. Similar plots are obtained with the other subjects of Example 29, demonstrating a close in vivo approximation of zero order absorption achieved with the aspirin formulations of the present invention.

EXAMPLE 35

Comparative Bioavailability Study

An open, single-dose crossover study was conducted in ten subjects, comparing aspirin tablets formulated according to Example 7 and standard formulated aspirin. Two-800 mg tablets were given of each formulation as a single dose. Blood samples were taken at specified times over a thirty-two-hour period following the administration of either drug, and analyzed for acetylsalicylic acid, (ASA) salicylic acid (SA) and the prostaglandin, $PGE_2$.

The analysis of the blood samples showed that SA blood levels were prolonged following the administration of aspirin tablets formulated in accordance with Example 7, as compared to standard formulated aspirin. Additionally $PGE_2$ blood levels were suppressed for as long as fourteen hours after the administration of the Example 7 formulation as compared to six hours when the subjects received the standard aspirin formulation.

EXAMPLE 36

Comparative Efficacy Study

An eight-week, double-blind, parallel comparison was made of the safety and efficacy of aspirin tablets formulated in accordance with Example 7 (Group I, 21 patients) and sulindac (Group II, 20 patients) for the treatment of patients with osteoarthritis. Patients in Group I received 2-800 mg tablets twice-a-day, of the Example 7 formulation, and Group II received 1-150 mg tablet, twice-a-day, of sulindac. The patients were evaluated to determine efficacy and clinical safety of the drugs.

The results of this body revealed that both drugs were equally effective in the treatment of osteoarthritis. Also, the clinical safety of both drugs was similar.

Therefore, the results of this study indicate that aspirin tablets formulated in accordance with Example 7 are as safe and effective as one of the widely used nonsteroidal anti-inflammatory drugs (sulindac).

EXAMPLE 37

Comparative Efficacy Study

A six-week, double-blind parallel comparison was made of the safety and efficacy of aspirin tablets formulated in accordance with Example 7 (Group I, 26 patients) and standard formulated aspirin tablets (Group II, 25 patients) for the treatment of patients with osteoarthritis. Patients in Group I received 2-800 mg tablets, twice-a-day, of the Example 7 formulation, and Group II received 1-800 mg tablets, four-times-a-day, of the standard aspirin formulation. The patients were evaluated to determine efficacy and clinical safety of the aspirin formulations.

As expected, the results of the study showed that both aspirin formulations were equally effective in the treatment of osteoarthritis. However, only 38% of the patients who received aspirin tablets of the Example 7 formulation reported having side effects, as compared to 65% of the patients who received the standard aspirin formulation.

EXAMPLE 38

Ibuprofen Tablets—400 mg

A solution of release-controlling agent of the following composition was prepared
Cellulose acetate phthalate: 50 g
Ethanol (denatured): 620 ml
Methylene chloride: 250 ml The cellulose acetate phthalate was added slowly to the vortex of the solvents produced by a high speed stirrer and stirring continued until solution was achieved.

Ibuprofen (British Pharmacopeia Viz., 2-(4-isobutylphenyl)-propionic acid) 2.5 kg, Encompress (TM) special (dicalcium phosphate dihydrate) 0.75 kg, and corn starch, USP 0.155 kg were deaggregated through a 30 mesh/inch stainless steel screen into the bowl of a Hobart mixer. The dry powders were mixed for five minutes at speed 1.

The solution of cellulose acetate phthalate was added to the mixing powders (speed 1) over a period of thirty seconds and mixing was continued at speed 1 for a further thirty seconds. At this time, the powder mass was wetted out and further mixing at speed 2 for three minutes was carried out to promote granule formation. This wet granular mass was discharged onto stainless steel trays and air dried until the mass could be forced through a stainless steel screen of 14 meshes per inch. The screened granulate was further air dried until no odor of solvent was detectable and the weight loss on drying was less than 1.3%. The granules were weighed and the quantity of colloidal silicon dioxide (Aerosil 200-TM) at 0.5% was calculated as 0.017 kg. A quantity of dried granule of about 0.05 kg was withdrawn from the bulk and blended with the colloidal silicon. This preblend was then mixed with the bulk of the granules in the Hobart mixer for ten minutes at speed 1.

The blended granules were obtained in a yield of 98.4%. The flow properties of the granules assessed by the method of Carr (Brit. Chem. Eng. 15, 1541–1549, 1970) were found to be fair to passable.

The granules were compressed on a conventional rotary tablet press using half-inch flat-bevelled edge tooling to give tablets containing 400 mg of ibuprofen with a hardness from 8 to 12 kp (Schleuniger).

The CF for this example is 155 and the percent by weight of release-controlling agent and erosion promoting agent 1.44 and 4.46, respectively.

| Tablet | Hardness kp | Disintegration Time(min) pH 7.5 buffer |
|---|---|---|
| Example 38 | 4.14 | 235–275 |
|  | 8.54 | 275–314 |

Disintegration of the tablets in buffer of pH 7.5 is characterized by a slow and steady erosion of the tablet mass. A conventional uncoated ibuprofen tablet disintegrates in less than sixty seconds and, when sugar coated, between five and ten minutes.

The in vitro dissolution, using apparatus 1 according to USP XX, page 959, of a tablet prepared as in Example 38 is illustrated below. Comparative data for a conventional marketed tablet of ibuprofen is also given.

| Tablet | Tablet Hardness (kp) | Amount* (mg) ibuprofen dissolved at times shown (min) | | | | | | | T50% (min) |
|---|---|---|---|---|---|---|---|---|---|
| | | 10 | 20 | 30 | 60 | 120 | 180 | 240 | |
| Ibuprofen 400 mg conventional | — | 112 | 300 | 358 | 417 | — | — | — | 13 |
| Ibuprofen 400 mg (Example 38) | 10.9 | — | — | 68 | 100 | 169 | 219 | 265 | 155 |

*Mean of 6 tablets
T50% = time for 50% of the ibuprofen dose to dissolve.

The range of ibuprofen in a tablet of the invention is preferably about 400 to 600 mg per tablet.

EXAMPLE 39

Disintegration and Dissolution Testing; Product Stability

Disintegration, by the method of the USP XX, page 958 but without disks, of tablets formulated as in Example 38 in simulated gastric juice (pH 1.2 buffer plus pepsin) at 37° C. leaves a residue of between 96 and 99% of the total tablet weight after two hours. Disintegration of formulations of Example 38 in a buffer of pH 7.5 at 37° C. gave the following results:

| Tablet | Mean Disintegration Time(min) | Residue % | Tablet Hardness (kp) |
|---|---|---|---|
| Example 38 | >240 | 12.8 | 10.86 ± 1.41 |

Tablets of ibuprofen manufactured according to Example 38 compressed to different hardnesses showed sustained release behavior over the range tested, illustrating the non-dependence of the formulation on compaction pressure. This facilitates routine production since machine-induced hardness variation does not substantially affect tablet disintegration performance.

The data for tablets of the type herein described show zero order release in vitro, since the data when plotted as a graph of time (abscissa) versus amount of ibuprofen dissolved (ordinate) gives a straight line and, when subjected to linear regression analysis, gives a correlation coefficient of 0.996 compared to 1.0 for a straight line.

Product Stability

An enhanced stability for products formulated in the manner described is illustrated by data for tablets formulated as in Example 38. There is no significant change in dissolution behavior following storage under extreme conditions, whereas conventional tablets show a change.

| Tablet | Storage Time and Location | Amount ibuprofen (mg)$^x$ dissolved at time shown(min) | | | | | | | T50% (min) |
|---|---|---|---|---|---|---|---|---|---|
| | | 10 | 20 | 30 | 60 | 120 | 180 | 240 | |
| Example 38+ | initial | — | — | 68 | 100 | 169 | 219 | 265 | 155 |
| | 3 mo 40° C. | — | — | 63 | 99 | 163 | 217 | 274 | 153 |
| Conventional Ibuprofen tablet* | initial | 277 | 318 | 365 | 383 | — | — | — | 8.4 |
| | 3 mo 40° C. | 62 | 110 | 163 | 248 | — | — | — | 41.3 |

$^x$Mean of 6 replicates
+pH 7.5 buffer dissolution
*pH 6.8 buffer dissolution
T50% = time for 50% of the ibuprofen dose to dissolve

EXAMPLE 40

Flurbiprofen Tablets—300 mg.

A solution of release-controlling agent of the following composition was prepared as in Example 1
Cellulose acetate phthalate: 9 g
Ethanol (denatured): 60 ml
Methylene chloride: 60 ml
Flurbiprofen (2-(2-fluoro-4-biphenylyl) propionic acid), 300 g, Emcompress(TM) special 240 g, and corn starch, USP 18.6 g were deaggregated through a screen of 30 meshes per inch into a mixing bowl. The dry powders were well mixed.

The solution of cellulose acetate phthalate was poured onto the powders and mixing continued until a wet granular mass was formed. The wet mass was air dried on a stainless steel tray until it could be forced through a screen of 16 meshes per inch. The screened granulate was further dried until no odor of organic solvent was detectable. The dried granule was weighed and the quantity of magnesium stearate equivalent to 0.5% by weight of the granules was calculated. The magnesium stearate 2.79 g was blended with the granules by tumbling.

The blended granules were compressed on a rotary tablet press to give tablets containing 300 mg of flurbiprofen at a hardness from 7 to 10 Kp (Schleuniger).

The CF for this example is 25 and the percent by weight of release-controlling agent and erosion-promoting agent are 1.58 and 3.26, respectively. The range of flurbiprofen in a tablet of the invention is preferably about 100 to 300 mg per tablet.

EXAMPLE 41

Disintegration Data

Disintegration, by the method of the USP XX, page 958 but without disks, of tablets formulated as in Example 40 in simulated gastric juice (pH 1.2 buffer plus pepsin) at 37° C. leaves a residue of between 83 and 85% of tablet weight after two hours.

Disintegration, by the method of the USP XX, page 958 but without disks, of tablets formulated as in Example 40 in a buffer of pH 7.5 gave the result shown:

| Sample | Mean Disintegration Time(min) | Residue % | Tablet Hardness (kp) |
|---|---|---|---|
| Example 40 | >300 | 3.7 | 8.69 ± 1.2 |

EXAMPLE 42

Dissolution Data

The dissolution of flurbiprofen from tablets prepared as in Example 40, assessed using apparatus 1 of USP XX page 959, in a phosphate buffer of pH 6.8, is shown below:

| Time (hrs) | Flurbiprofen dissolved* (%) |
|---|---|
| 1 | 9.6 |
| 2 | 22.5 |
| 3 | 29.3 |
| 4 | 34.8 |
| 5 | 44.8 |
| 7 | 56.9 |
| 10 | 74.0 |

*Mean of six tablets

Application of linear regression analysis to the data gives a correlation coefficient of 0.993 compared to 1.0 for a straight line. This indicates that a zero order mechanism is operating in the release of the medicament.

EXAMPLE 43

Flurbiprofen Tablets—100 mg.

A solution of release-controlling agent of the following composition was prepared as in Example 1.

Cellulose acetate phthalate: 8.33 g
Ethanol (denatured): 55 ml
Methylene chloride: 55 ml Flurbiprofen 100 g, Emcompress(TM) special 400 g, and corn starch 17.2 g were deaggregated and mixed as in Example 40.

The solution of release-controlling agent was added to the powders to form granules as in Example 40. The dried granules were blended as in Example 40 and compressed to give 100 mg of flurbiprofen per tablet at a hardness of 6 to 9 Kp (Schleuniger).

CF for this example is 25. The percent by weight content of release-controlling agent is 1.58 and of erosion-promoting agent is 3.26.

EXAMPLE 44

Disintegration Data

Disintegration, by the method of the USP XX, page 958, but without disks, of tablets formulated as in Example 43 in simulated gastric juice (pH 1.2 buffer plus pepsin) at 37° C., leaves a residue of between 63 and 67% of tablet weight after two hours.

Disintegration, by the method of the USP XX, page 958, but without disks, of tablets formulated as in Example 43 in a buffer of pH 7.5, gave the results shown below:

| Sample | Mean Disintegration Time(min) | Residue % | Tablet Hardness (Kp) |
|---|---|---|---|
| Example 43 | >360 | 4.9 | 7.14 ± 0.54 |

A conventional flurbiprofen 100 mg tablet subjected to a disintegration test in water at 37° C. gives a disintegration time of between five and twenty minutes.

EXAMPLE 45

Dissolution Data

The dissolution of flurbiprofen from tablets prepared as in Example 43, assessed using apparatus 1 of USP XX, page 959, in a phosphate buffer of pH 6.8 is shown below:

| Time (hrs) | Flurbiprofen dissolved* (%) |
|---|---|
| 1 | 10.6 |
| 2 | 17.1 |
| 3 | 24.7 |
| 4 | 28.8 |
| 5 | 35.1 |
| 7 | 47.7 |
| 10 | 68.5 |

*Mean of six tablets

Application of linear regression analysis to the data gives a correlation coefficient of 0.999 compared to 1.0 for a straight line. This indicates that a zero order mechanism is operating in the release of the medicament.

A conventional flurbiprofen 100 mg tablet assessed by the same dissolution test shows dissolution of the total dose of flurbiprofen in about one hour.

EXAMPLE 46

Aspirin Tablet-800 mg-Dissolution Data

A tablet prepared as in Example 7 was subjected to an in vitro dissolution test according to USP XX, page 959, using apparatus 1, with the following results:

| Time of sample(hr) | Acetylsalicylic acid dissolved (%) |
|---|---|
| 0.5 | 23.8 |
| 1 | 34.8 |
| 2 | 61.3 |
| 3 | 82.4 |

These results, when plotted as a graph of time (abscissa) versus percent acetylsalicylic acid dissolved (ordinate), give a straight line indicative of zero order release. Linear regression analysis of the data gives a correlation coefficient of 0.999, compared to a straight line value of 1.0.

Although the foregoing Examples evidence the application of the present invention to various orally-active therapeutic agents or medicaments to provide controlled-release tablets thereof, the invention is not limited to the tableting of the specific medicaments of the Examples. In this aspect, the invention can be varied widely and is applicable for the controlled-release tableting of an effective amount of any orally active medicament, although is preferably in the tableting of medicaments of an acidic nature, especially aspirin and non-steroidal arylalkanoic acid anti-inflammatory agents, including their salts, esters, anhydrides, and other derivatives, as previously disclosed. These compounds are antipyretics, analgesics, and anti-inflammatory agents. Other representative types of orally active medicaments which may be controlled-release tableted according to the invention include sedatives, stimulants, antibiotics, antispasmodics, nutritional agents, hematinics, anthelmintics, expectorants, hormones of various types including adrenocorticosteroids, androgenic steroids, estrogenic steroids, progestational steroids, and anabolic steroids, nonsteroidal counterparts of the foregoing, psychic energizers, antiviral agents, and the like, of all of which types numerous specific embodiments are well known and will be both readily apparent and readily available to one skilled in the art.

It is to be understood that the invention is not to be limited to the exact details of operation or exact compounds, compositions, methods, or procedures shown and described, as obvious modifications and equivalents will be apparent to one skilled in the art.

We claim:

1. A compressed, controlled-release tablet suitable for oral administration, said tablet consisting essentially of an effective amount of an orally-active therapeutic agent selected from aspirin and a nonsteroidal arylalkanoic anti-inflammatory agent, a release-controlling agent, and an erosion-promoting agent, in proportions which provide a criticality factor between 20 and 450, calculated according to the formula:

$$CA/(1/CS) = CF$$

wherein: CA is the milligram per tablet content of therapeutic agent divided by the milligram per tablet content of release-controlling agent, CS is the milligram per tablet content of erosion-promoting agent divided by the milligram per tablet content of release-controlling agent, and CF is the criticality factor, said proportions including 0.8 to 1.6 weight percent per tablet of said release-controlling agent and 1.0 to 7.5 weight percent per tablet of said erosion-promoting agent, wherein the release-controlling agent is selected from the group consisting of cellulose acetate phthalate, cellulose acetate derivatives, shellac, zein, acrylic resins, ethylcellulose, hydroxypropylmethylcellulose phthalate, sandarac, and modified shellac; and wherein the erosion-promoting agent is selected from the group consisting of corn starch, rice starch, potato starch and other vegetable starches, modified starch, starch derivatives, cellulose, cellulose derivatives, modified cellulose, modified cellulose derivatives, alginic acid, alginates, bentonite, veagum, cross-linked polyvinyl pyrrolidone, ion exchange resins, and gums.

2. The tablet of claim 1 wherein the criticality factor is 80–330.

3. The tablet of claim 1 wherein the criticality factor is 210–330.

4. The tablet of claim 1 wherein said release-controlling agent is cellulose acetate phthalate.

5. The tablet of claim 1 wherein said erosion-promoting agent is corn starch.

6. The tablet of claim 2 wherein said release-controlling agent is cellulose acetate phthalate and said erosion-promoting agent is corn starch.

7. The tablet of claim 1 wherein said therapeutic agent is aspirin.

8. The tablet of claim 2 wherein said therapeutic agent is aspirin.

9. The tablet of claim 3 wherein said therapeutic agent is aspirin.

10. The tablet of claim 4 wherein said therapeutic agent is aspirin.

11. The tablet of claim 5 wherein said therapeutic agent is aspirin.

12. The tablet of claim 6 wherein said therapeutic agent is aspirin.

13. The tablet of claim 1 wherein said therapeutic agent is 650 to about 800 mg of aspirin.

14. The tablet of claim 4 wherein said therapeutic agent is 650 to about 800 mg of aspirin.

15. The tablet of claim 5 wherein said therapeutic agent is 650 to about 800 mg of aspirin.

16. The tablet of claim 6 wherein said therapeutic agent is 650 to about 800 mg of aspirin.

17. The tablet of claim 1 wherein said therapeutic agent is a nonsteroidal arylalkanoic anti-inflammatory agent.

18. The tablet of claim 2 wherein said therapeutic agent is 400–600 mg of ibuprofen.

19. The tablet of claim 1 wherein said therapeutic agent is 100–300 mg of flurbiprofen.

20. The tablet of claim 17, wherein said release control agent is cellulose acetate phthalate.

21. The tablet of claim 18, wherein said release control agent is cellulose acetate phthalate.

22. The tablet of claim 19, wherein said release control agent is cellulose acetate phthalate.

23. The tablet of claim 17, wherein said release control agent is cellulose acetate phthalate and said erosion-promoting agent is starch.

24. The tablet of claim 18, wherein said release control agent is cellulose acetate phthalate and said erosion-promoting agent is corn starch.

25. The tablet of claim 19, wherein said release control agent is cellulose acetate phthalate and said erosion-promoting agent is corn starch.

* * * * *

UNITED STATES PATENT AND TRADEMARK OFFICE
CERTIFICATE OF CORRECTION

PATENT NO. : 4,308,251

DATED : December 29, 1981

INVENTOR(S) : James M. Dunn and John F. Lampard

It is certified that error appears in the above—identified patent and that said Letters Patent is hereby corrected as shown below:

[73] ASSIGNEE; change "Nottingham, England" to read -- Shreveport, LA --
Col. 1, line 46; "anhydricde" should read -- anhydride --
Col. 2, line 5; "canot" should read -- cannot --
Col. 2, line 43; "irritaion" should read -- irritation --
Col. 2, line 65; "provie" should read -- provide --
Col. 3, line 1; "Gun" should read -- Guy --
Col. 3, line 37; "provie" should read -- provide --
Col. 4, line 8 & 9; "formuation" should read -- formulation --
Col. 4, line 17; "m" should read -- mg --
Col. 4, line 38; "grahical" should read -- graphical --
Col. 4, line 38; the "st" in "illustration" is smudged.
Col. 5, line 4; "cricitcality" should read -- criticality --
Col. 5, line 51; "non-chlorinatedhydrocarbons" should read
  -- non-chlorinated hydrocarbons --
Col. 8, line 39 (footnote of Table 3); "acetylsalicyllic" should read
  -- acetylsalicylic --
Col. 9, Table 6 should have a -- 26. -- over by the left hand margin, near the 3rd line of the table.

UNITED STATES PATENT AND TRADEMARK OFFICE
CERTIFICATE OF CORRECTION

PATENT NO. : 4,308,251

DATED : December 29, 1981

INVENTOR(S) : James M. Dunn and John F. Lampard

It is certified that error appears in the above—identified patent and that said Letters Patent is hereby corrected as shown below:

Col. 9, Table 6A should have a -- 27. -- over by the left hand margin, near the 3rd line of the table.
Col. 12, line 63; "Oral" should read -- Order --
Col. 14, line 7; "body" should read -- study --

Signed and Sealed this

First Day of June 1982

[SEAL]

*Attest:*

*Attesting Officer*

GERALD J. MOSSINGHOFF

*Commissioner of Patents and Trademarks*